US00RE48356E

(19) United States
(12) Reissued Patent
Searle et al.

(10) Patent Number: US RE48,356 E
(45) Date of Reissued Patent: Dec. 15, 2020

(54) AIR CANNON AND ASSOCIATED LAUNCH CANISTER FOR A LINE-FOULING SYSTEM

(71) Applicant: BCB International Limited, Cardiff (GB)

(72) Inventors: Matthew Searle, Bruton (GB); William Mark Hocking, South Glamorgan (GB); Andrew Rhys Howell, South Glamorgan (GB); Derek William Taylor, South Glamorgan (GB)

(73) Assignee: BCB INTERNATIONAL LIMITED, Cardiff (GB)

(21) Appl. No.: 16/149,781

(22) Filed: Oct. 2, 2018

Related U.S. Patent Documents

Reissue of:
(64) Patent No.: 10,030,943
Issued: Jul. 24, 2018
Appl. No.: 14/906,128
PCT Filed: Jun. 4, 2014
PCT No.: PCT/GB2014/051729
§ 371 (c)(1),
(2) Date: Jan. 19, 2016
PCT Pub. No.: WO2015/011437
PCT Pub. Date: Jan. 29, 2015

(30) Foreign Application Priority Data

Jul. 24, 2013 (GB) ..... 1313226.1

(51) Int. Cl.
*F41H 13/00* (2006.01)
*A63B 69/20* (2006.01)
(Continued)

(52) U.S. Cl.
CPC ..... *F41H 13/0006* (2013.01); *A61K 38/162* (2013.01); *A63B 69/208* (2013.01);
(Continued)

(58) Field of Classification Search
CPC ..... F41H 13/0006; F41H 11/05; B63B 21/48; B63B 21/22; G06F 11/3438;
(Continued)

(56) References Cited

U.S. PATENT DOCUMENTS 1,299,901 A 4/1919 Blair
4,799,906 A * 1/1989 Perkins, Jr. ..... B63C 9/22 102/504
(Continued)

FOREIGN PATENT DOCUMENTS

CN 201378015 Y 1/2010
DE 4437412 A1 9/1995
(Continued)

OTHER PUBLICATIONS

International Search Report and Written Opinion, as issued in connection with International Patent Application No. PCT/GB2014/051729, dated Jun. 24, 2015, 15 pgs.

*Primary Examiner* — Jeffrey L Gellner
(74) *Attorney, Agent, or Firm* — Maschoff Brennan

(57) ABSTRACT

FIG. 7 shows an air cannon system loaded with a launch canister containing a prop-fouler. A pressure vessel (28) contains an inlet including a poppet valve (100) that, upon command, can be selectively placed in either a one-way flow position to permit charging of the pressure vessel or otherwise opened to trigger rapid discharge through pressure equalization with the ambient environment. The air cannon may include multiple splayed barrels or a single barrel (158). A launch canister (202), realized in the form of a tube, has a driving plate (350) that closes an end of the launch tube. The driving plate is the first point loaded into the barrel. Within the launch canister (202) a first portion of a floating prop-fouling line is stored. The prop-fouling line, such as made from Dyneema®, has at its ends two drogues that, upon entry into the water, fill with water to produce drag
(Continued)

resistance to movement of the prop-fouling line. To avoid undue stress on canopy panels of each drogue and to avoid twisting of shroud lines (312) to the canopy, a rotating shackle (310a, 310b) acts as a coupling point between the shroud lines (312) and the prop-fouling line. Only one drogue (306), its associated coupling and a selected length prop-fouling line are loaded into the launch canister, with the other drogue and its rotating shackle (310b) loaded into a cradle (166). Upon firing, gas expansion causes the rapid acceleration and ejection of the launch tube (202) and generally straight line deployment of the prop-fouling line (302).

15 Claims, 6 Drawing Sheets

(51) Int. Cl.

| | |
|---|---|
| ***A61K 38/16*** | (2006.01) |
| ***A63B 71/00*** | (2006.01) |
| ***B63B 21/22*** | (2006.01) |
| ***B63B 21/48*** | (2006.01) |
| ***B63C 9/26*** | (2006.01) |
| ***F41B 11/62*** | (2013.01) |
| ***F41F 1/08*** | (2006.01) |
| ***F41H 11/05*** | (2006.01) |
| ***G06F 11/34*** | (2006.01) |
| *A63B 71/02* | (2006.01) |

(52) U.S. Cl.
CPC ..... *A63B 71/0036* (2013.01); *B63B 21/22* (2013.01); *B63B 21/48* (2013.01); *B63C 9/26* (2013.01); *F41B 11/62* (2013.01); *F41F 1/08* (2013.01); *F41H 11/05* (2013.01); *G06F 11/3419* (2013.01); *G06F 11/3438* (2013.01); *A63B 2071/025* (2013.01)

(58) Field of Classification Search
CPC .... G06G 11/3419; B63C 9/26; A61K 38/162; F41B 11/62; F41F 1/08; A63B 71/0036; A63B 69/208; A63B 207/025
See application file for complete search history.

(56) References Cited

U.S. PATENT DOCUMENTS

| | | | | | |
|---|---|---|---|---|---|
| 4,912,869 | A * | 4/1990 | Govett | F41C 7/00 | 42/105 |
| 5,450,839 | A | 9/1995 | Nicolaevich et al. | | |
| 5,584,736 | A * | 12/1996 | Salvemini | B63C 9/26 | 441/85 |
| 6,591,774 | B2 * | 7/2003 | Metherell | B63G 9/04 | 114/240 E |
| 7,401,565 | B2 * | 7/2008 | Nixon | F41H 11/05 | 114/240 C |
| 7,975,639 | B2 | 7/2011 | Bishop | | |
| 8,245,617 | B2 * | 8/2012 | Martinez | B63G 9/04 | 114/382 |
| 8,402,894 | B1 | 3/2013 | McGuigan | | |
| 9,080,832 | B2 * | 7/2015 | Brahler, II | F41B 11/723 | |
| 9,134,099 | B2 * | 9/2015 | Tseng | F41H 13/0006 | |
| 2002/0134365 | A1 * | 9/2002 | Gray | F41H 13/0006 | 124/56 |
| 2003/0051652 | A1 | 3/2003 | Metherell et al. | | |
| 2005/0016372 | A1 * | 1/2005 | Kilvert | F41H 13/0006 | 89/1.34 |
| 2012/0192707 | A1 * | 8/2012 | Rogers | F41H 11/02 | 89/36.08 |

FOREIGN PATENT DOCUMENTS

| | | | | |
|---|---|---|---|---|
| DE | 202007013115 | U1 | 12/2007 | |
| DE | 102008056099 | B3 | 9/2009 | |
| FR | 496796 | A | 11/1919 | |
| GB | 1321892 | | 7/1973 | |
| WO | 82/01860 | A1 | 6/1982 | |
| WO | 95/11724 | A1 | 5/1995 | |
| WO | 99/30966 | A1 | 6/1999 | |
| WO | WO 2012114559 | A1 * | 8/2012 | F41B 11/62 |

* cited by examiner

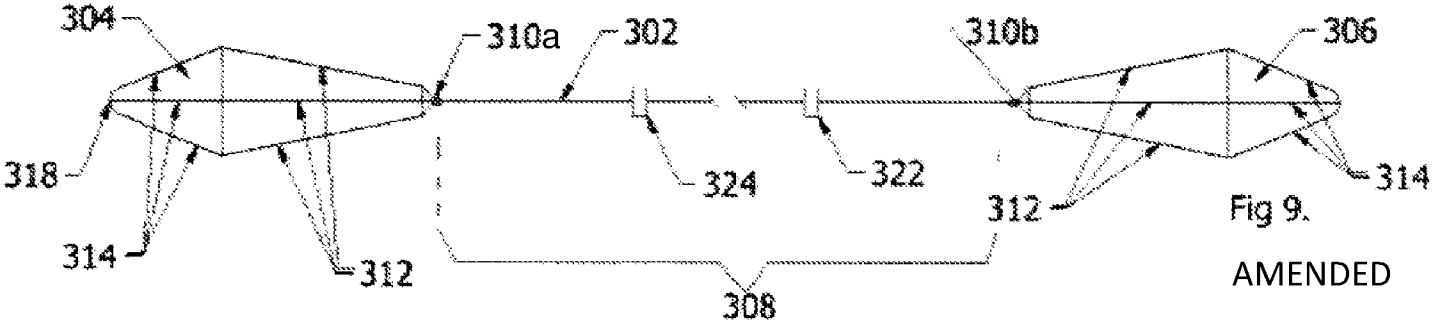
Fig 9.
AMENDED

AIR CANNON AND ASSOCIATED LAUNCH CANISTER FOR A LINE-FOULING SYSTEM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND TO THE INVENTION

This invention relates, in general, to an air cannons and is particularly, but not exclusively, applicable to air cannons in combination with a launch canisterthataids in deployment of a security cord or net (commonly referred to as a "prop-fouler") as a near-surface, floating security curtain.

SUMMARY OF THE PRIOR ART

With respect to the security policing of jetties, ships or more generally waterways, there is currently a two-level approach to fending off potential threats or active incursions launched from boats, dingys and the like. As an initial approach to a perceived boat-based threat, the security force (typically on a RIB or on-shore) shout a warning "to cease activity and move away". If this verbally delivered warning is ignored, then time is lost and the ante significantly increased through the threat and use of a lethal response where the navy/coastguard or police enter the fray 'with all guns blazing'. With no effective intermediate system and procedure that both keeps the security forces at a reasonably safe distance and maintains the perceived threat at an appropriate remote distance, security forces and property (or VIPs) are unnecessarily exposed to harm and damage.

Another issue arises with mounting, for example, any active device to a RIB. Specifically, a universal gun mount (UGM) is a steel bracket that supports a machinegun of the like. The UGM is mounted to a fibreglass-hulled RIB, so any recoil through the UGM has the potential to destroy the point of mechanical coupling of the UGM to the RIB.

Finally, storage, servicing and use of explosive-based anti-incursion systems requires specialist training and always a high degree of care. In the event that the explosive does not ignite or a complex firing mechanism jams, then the system is significantly compromised. Pyro-based systems therefore have severe limitations, not least because small explosive charges can only accelerate small masses over longer distances and large charges (required for heavy masses) are fundamentally dangerous and require robust, heavily engineered devices to resist the explosive forces.

DE202007013115U relates to a handheld and shoulder-mounted rocket launcher ("Raketenwerfer"). While a pressure imbalance permits air to exit a pressure vessel (see FIG. 4 relative to FIG. 6 of that document) around a piston at a point when a trigger handle moves shaft against securing spring, the generated recoil force is entirely absorbed by the body-mass of the operative. The firing mechanism includes multiple mechanically-released components perpendicularly mounted relative to the direction of fire.

US2002134365 provides for net-launching from a rifle that is held into the operator's shoulder. Force is generated from rapidly expanding developed from an explosive cartridge loaded into the rifle by a withdrawing bolt. The expanding gas is distributed between four (4) barrels via a manifold. A limited recoil mechanism is provided by a compression spring cooperating with a sleeve and rod. The device is designed to "capture live game" and its range and power are therefore highly limited.

WO95/11724 is a projectile firing device that comprises a reservoir for compressed gas and an outlet chamber connected to the reservoir via a primary fast response valve controlled by a trigger valve which is provided with a hammer device. The primary valve contains a seat provided with at least two annular ledges separated by a space and forming an annular flow-through duct between the reservoir and the outlet chamber, the said duct narrowing towards the latter; a hollow cylindrical body provided with an outlet aperture on the same side as the flow-through annular duct and coaxial with it; and a displaceable splitter mounted telescopically on the cylindrical body on the same side as the outlet aperture. The trigger valve comprises a first chamber which communicates with the hollow space inside the cylindrical body of the primary valve; a second chamber which communicates with the atmosphere; a flow-through annular duct between chambers, tapering in the direction from the first chamber towards the second chamber, and provided with at least two annular ledges separated by a space, the said ledges forming a seat; a hollow cylindrical body which is mounted in the first chamber, connected via a reduction valve to the compressed gas source and via the hammer device to the atmosphere, and provided with an outlet aperture and a displaceable splitter mounted telescopically on the cylindrical body on the same side as the outlet aperture. This configuration can therefore be categorised as a handheld, low-powered and single-barrelled device, with a complex mechanical actuations and no mechanical recoil mechanism, with the system relatively low-powered and handheld.

U.S. Pat. No. 5,450,839 is another handheld pneumatic system with no active recoil mechanism. The device finds application is a life-line launcher. A cylindrical storage member and a cylindrical barrel are coaxial, with a cylindrical body therebetween. Pressurized gas is coupled into the chamber of the body. A valve member has a sleeve portion which telescopically receives the cylindrical body. The gas entering the chamber leaks through the space between the sleeve portion and the body to fill the reservoir. The valve member has a second valve portion which is conical and movable against a valve seat. When it is desired to launch a projectile in the barrel, gas is exhausted from the chamber causing the valve member to snap back to its opened condition almost instantaneously to deliver gas from the reservoir to the barrel, thereby to launch the projectile therein. Effectively, a pressure differential is established when a passageway is opened, with this causing a valve member to disengage from valve seat. Gas stored in a reservoir then passes through passageway and into a single bore.

WO82/01860 describes a launching apparatus for discharging a projectile connected to a lifeline or the like. The apparatus comprises a launching tube which is connected to a source of compressed air via a main valve having rapid valve movement. In connection with the launching tube, a reservoir for compressed air is provided. The main valve is arranged between the reservoir and the launching tube and has a large flow area. The valve is actuated into an open position by means of a pressure-driven servomechanism which consists of a cylinder and a piston which is connected to the main valve. Inlets for compressed air into the cylinder space in back of the piston are provided, a manually-operable valve in the non-actuated position holding said inlet open. On the back side of the piston a compression spring is arranged which pushes the piston and thereby the main valve into the closed position. The manually-operable valve has an air drain passage from the cylinder space in back of the piston which is opened when the manual valve is actuated while at the same time the inlet is closed, such that the pressure in back of the piston disappears and the piston is pushed back, the front side of the piston being open toward the compressed air reservoir. A projectile means for a launching apparatus for lifelines, especially an air-driven launching apparatus, has a rearwardly-open compartment provided in the projectile for receiving and containing the necessary length of line. The line is arranged inside the compartment in loops running back and forth, layer upon layer, inside the compartment. The compartment can be closed by means of an easily removable lid, to prevent air pressure from entering the compartment when the projectile is fired. An apparatus for placing the line inside the projectile consists of a tube having a bore diameter which is somewhat larger than the cross-sectional diameter of the line. One end of the tube is connected to a chamber having a somewhat larger inside diameter than that of the tube. A laterally-directed opening is provided in the exterior of the chamber for introducing the line thereinto, and an inlet for admitting compressed air into the chamber is arranged above the inlet end of the tube. A perforated plate can be provided at the free end of the tube, the primary plane of said plate lying transversely of the longitudinal axis of the tube. This plate is utilized when the line is being inserted into the projectile, for compressing the line. Unlike other designs, the lifeline is actually coiled in the nose-cone and is thus deployed rearwardly from the projectile. A rearward end of the line is fastened to lid which prevents air pressure from entering compartment during firing. In sum, this device looks to send a lifeline to a specific point.

U.S. Pat. No. 1,299,901 describes an air-gun that expels a shot using compressed air. A piston disengages from a seat to allow egress of compressed air from pressure vessel. There's no recoil for this handheld device; recoil is simply absorbed because of the low pressures arising from its field of application.

CN201378015Y apparently relates to a single-barrelled air launcher that utilizes a valve and a pressure reservoir.

DE102008056099 is another single-barrelled configuration that makes use of a piston to cause a medium to be discharged into the barrel. The cannon has a piston arranged in a working medium chamber and shifted on a tubular body and partially impinging the medium chamber. The piston is brought under pressure of a working medium in an area of closure valves between the medium chamber and a propellant chamber in an end position. The piston causes discharge of the medium from the medium chamber into the body under pressure of a propellant. The piston is moved into another end position, where the propellant is withdrawn in the latter end position by a passage opening into the tubular body. An independent claim is also included for a method for operating a universal cannon.

U.S. Pat. No. 4,912,869 a pyro-based net gun system that effectively adapts a rifle butt and stock arrangement by mounting a 4-barrel muzzle. In this pyro-based device, there's no active recoil mechanism. A stock, an action member, a firing chamber, a manifold and a plurality of barrels are connected to the manifold. Each of the barrels is adapted to receive a projectile which has an inner bore that is closely fitted over the external diameter of the barrel. Each barrel has a restrictor at the manifold end. A plurality of apertures are formed through the wall of the projectile adjacent to the barrel. The system provides for the distribution of a net to catch a live animal.

GB1321892 adopts a slightly different approach in which loading of a mortar-like projectile actuates the firing mechanism, as shown in FIGS. 1 and 3. Essentially, recoil is absorbed because of the ground-mounted nature of this "mortar", so recoil is not an issue for this line projecting, compressed-air mooring line application. A gas powered line projecting gun arranged to eject a projectile containing a contact line coupled to a grapnel assembly comprises means which is tripped by the insertion of the projectile into the barrel of the gun and by which when tripped the supply of compressed air to a chamber of the gun is cut-off and the compressed air in the chamber is applied to the projectile to eject the projectile from the gun. In the construction shown a main valve forming part of the valve assembly closes the chamber from the barrel, the pressure on the valve being partly balanced by the pressure on a balance valve and the valve being held in its cocked position by the co-operation of a D-shaped cam on a rotatable shaft with an abutment on the shaft of the main valve. The cam carrying shaft is operatively connected through a lever and link to a normally open valve in the barrel, the projectile closing the normally open valve during its insertion into the barrel, rotating the cam and releasing the main valve. A cocking lever which co-operates with a button on the main valve shaft is provided.

Furthermore, high speed boats are difficult to stop, especially if it is desired to not damage the boat or occupants during an enforced stop. For example, it may be necessary to stop a boat because the driver has fallen out of the boat or because law enforcement authorities wish to stop the vessel. Previous systems, such as the US Coast Guard SNARE, U.S. Pat. No. 8,402,894 and other systems (such as described in U.S. Pat. No. 7,975,639) have tried to entangle the propeller of a craft. However, entangling a propeller (i.e. "prop fouling") is not easy. To date, a single line does not work very well as an entanglement device, whilst nets perform relatively well. However, nets are made up from multiple lines and are consequently heavy and hard to deploy, Nets therefore need either a large launcher or else they have to be kept unacceptably short to be able to be launched from a hand held device.

SUMMARY OF THE INVENTION

According to a first aspect of the invention there is provided a floating boat fouling line having first and second ends, the floating boat fouling line comprising: a length of high-strength, lightweight cord defining the first and second ends and a central section of the boat fouling line; a first rotating shackle and a second rotating shackle, the first rotating shackle coupled to the first end of the cord and the second rotating shackle coupled to the second end of the cord; at least two drogues each having multiple shroud lines extending from a canopy thereof; wherein the shroud lines from a front drogue are attached to the first rotating shackle and shroud lines from a tail drogue are attached to the second rotating shackle, the rotating shackles both acting as a sink weight to cause, when deployed in water, submersion of each respective canopy and to isolate twisting of the central section of the high-strength cord from twisting of said shroud lines 312 and/or closure of said canopy of each drogue.

Preferably, the floating boat fouling line further includes: a front float coupled high-strength, lightweight cord and in relative close proximity to the first rotating shackle and inbound of the first rotating shackle relative to the front drogue; and a second float coupled to the high-strength, lightweight cord and in relative close proximity to the second rotating shackle and inbound of the second rotating shackle relative to the tail drogue.

In a second aspect of the invention there is provided a launch canister delivery system comprising: a sleeve configured to fit within a barrel of an air cannon, the sleeve having a closed end and an open end, the closed end including a driving disk configured as a reaction plate upon which high velocity pressurised air can act to propel the launch canister delivery system; the sleeve packed with a part of the floating boat fouling line of claim 1, the packed part being the front drogue, the first rotating shackle and a portion of the central section of the high-strength cord.

The sleeve may include at least one and preferably a plurality of ventilation holes juxtaposed the driving disk.

In the launch canister delivery system, the front drogue is preferably loaded closest the drive plate and the portion of the central section of the high-strength cord loaded between the first rotating shackle and the open end of the tube. A major part of the length of the high-strength cord or stored is inside the sleeve whereas both a minor length of the high-strength cord and the second end of the high-strength cord are located externally to the launch canister delivery system.

The boat stopping system of the preferred embodiment makes use of a floating line with sea anchor drogues at either end. The drogues are both projected away from an operator of an air cannon by, on the one hand, positive air pressure and, on the other hand, a dragging effect when line extension is reached. The system therefore provides a rapidly deployable boat stopping system having a tactically useful length of prop fouler.

In another aspect of the invention there is provided an air cannon (150) including: a first barrel containing the launch canister delivery system of any of claims 6 to 10, the barrel including a muzzle end and a manifold end, the closed end of the sleeve loaded into the barrel so that the driving plate is seated adjacent the manifold end; and a pressure vessel for storing pressurised gas, the pressure vessel in fluid communication with the manifold end of the first barrel, the pressure vessel connected to the first barrel through a valve controllably opened to allow, after charging and firing, rapid expansion of pressurized gas from the pressure vessel to impinge on the driving plate of the sleeve to accelerate the launch canister delivery system out of the first barrel.

In a preferred embodiment, a cradle is coupled to the barrel, wherein a major part of the length of the high-strength cord is stored inside the sleeve and both a minor length of the high-strength cord and the second end of the high-strength cord are loaded into the cradle.

The launch canister delivery system is packed with a front float positioned adjacent the first rotating shackle and inbound of the first rotating shackle relative to the front drogue;

The cradle may be a secondary barrel located beneath the first barrel, the secondary barrel having an open end and a closed end and wherein the secondary barrel is packed with the tail drogue loaded closest to the closed end of the secondary barrel. The secondary barrel is packed with a second float coupled to the high-strength, lightweight cord, the second float in close proximity to the second rotating shackle and inbound of the second rotating shackle relative to the tail drogue.

Once fired and separated from the launch canister, the masses associated with the floats and rotating shackles have forward momentum that maintains a projectile/deployment path as generally straight.

In yet another aspect of the invention there is provided a multi-barrelled air-cannon comprising: at least first and second barrels each having a muzzle end and each commonly sharing a breech chamber, said first barrel angled relative to said second barrel; a pressure vessel containing: an inlet including a valve that, upon command, can be selectively placed in either a one-way flow position to permit charging of the pressure vessel or otherwise opened to trigger discharge; a piston moveable within a volume defined by an internal sleeve within the pressure vessel, the internal sleeve in fluid communication with the inlet and its valve, the piston having an inner surface and an outer surface including an outward facing contact region, the outward contact region abutting and sealing, in use, against a wall of the pressure vessel when the pressure vessel is pressurised and the piston located in a closed position, the outward contract region and the piston further cooperating as a poppet valve actuated when the valve of the inlet is briefly opened to produce a local pressure differential across the piston by producing a relatively lower pressure within the volume of the internal sleeve relative to an instantaneous pressure acting on the outer surface, the differential pressure sufficient to cause the piston to move and disengage from the wall; and an outlet channel coupling the breech chamber to the pressure vessel, the outlet channel defined by a passageway formed by at least the outer surface of the piston and the wall.

A recoil mitigation system may be coupled externally to the pressure vessel.

Typically, the pressure vessel has a volume of between about 3000 $cm^3$ and about 6000 $cm^3$ that realizes a kinetic energy of between about 10 kN and 50 kN for a shot weight of between about 2 kg and 7 kg. Other sizes are considered, with size dependent upon delivery of the security curtain or fouling line.

In yet another aspect of the present invention there is provided a net-launching system comprising: the multi-barrelled air-cannon of any of claims 16 to 20; and an expandable net stored within a payload storage compartment beneath said at least said first and second barrels, the net tethered at opposing ends thereof to a plurality of shot weights each respectively loadable into selected ones of said barrels.

The air-cannon is capable of being mounted on a RIB since an active recoil mechanism limits force conveyed directly into its mount. The launch canister of the preferred embodiment ensures that a remote end of the prop fouler is projected away from the point of firing to as to ensure that deployment of the prop fouling line occurs under tension and such that a generally straight-line deployment of the prop fouler is achieved. Advantageously, embodiments of the present invention provide a net-launcher that is mechanically optimized in terms of its configuration and number of interacting parts to effect deployment of an effective security cordon/curtain over a large area in a quick, repeatable and safe fashion from a universal gun mount that is not conventionally designed to dissipate recoil.

Smaller air cannon variants can be shoulder-supported.

Beneficially, the systems and embodiments of the present invention are both easy to charge and reload.

The amount of pressure generated (especially in the multi-barreled embodiments) may be significant and can simultaneously launch two drag weights over distances of several hundred meters, the drag weights coupled together by a netting that is, typically, up to about two hundred meters across and several meters deep. The resultant security curtain can there act as a propeller-fouler. To mitigate the potential damage to a RIB to which the air cannon is coupled (via a UGM), the air cannon is preferably made from lightweight or composite materials and fitted with an active recoil mechanism.

The technologies of the various aspects of the invention find particular application in policing and particularly shoreline defense. Firing of the system causes a folded net (stored beneath the barrels and attached via tethers to the shot slugs or projectiles) to be pulled out and thus to expand outwardly to produce a physical curtain that lays at least on the surface of the water, but preferably lies a little beneath the surface of the water and which is weighted downwards. This system therefore provides a much-needed intermediate approach between the shouted verbal warning and lethal force.

BRIEF DESCRIPTION OF THE DRAWINGS

Exemplary embodiments of the present invention will now be described with reference to the accompanying drawings, in which:

FIG. 9 shows a preferred configuration of a prop fouler according to the present invention.

DETAILED DESCRIPTION OF A PREFERRED EMBODIMENT

Figure 1:
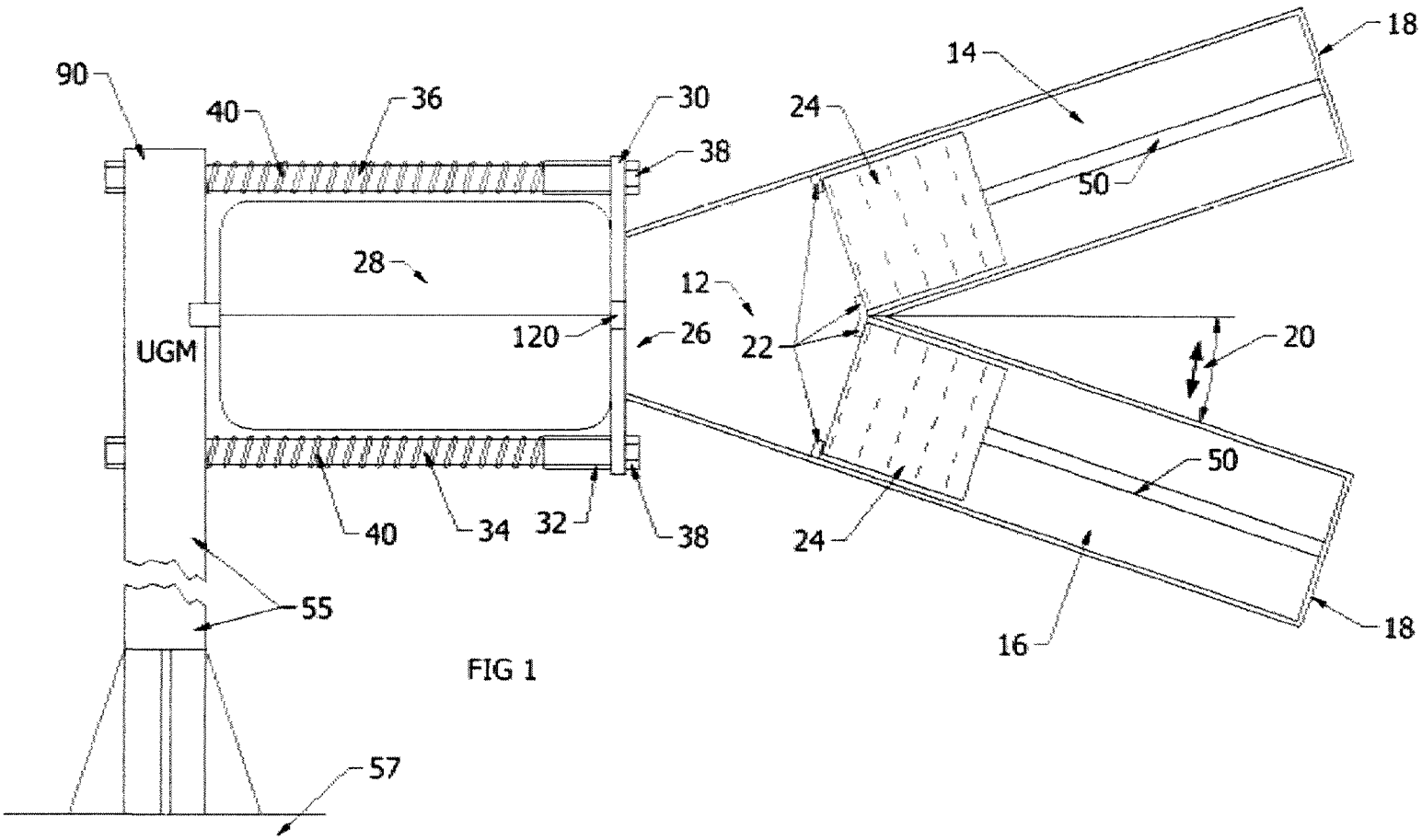
FIG. 1 is a schematic plan view of a multi-barrelled air cannon of a preferred embodiment of the present invention.
Figure 2:
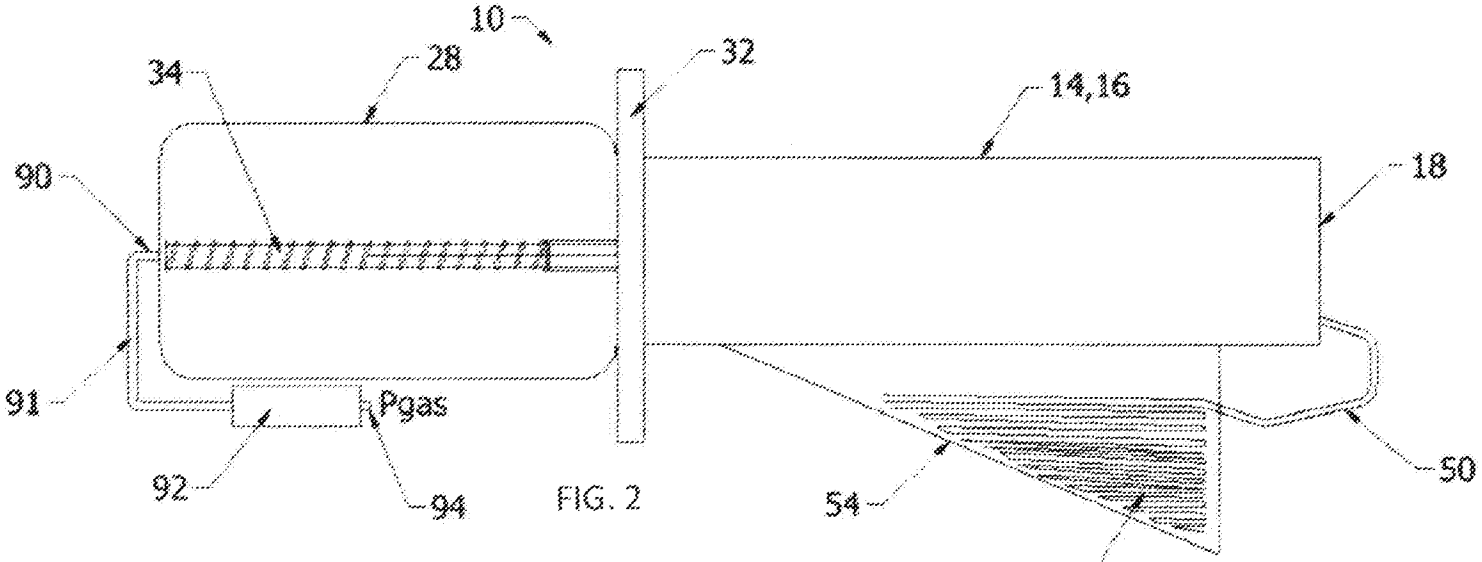
FIG. 2 is a schematic side view of the multi-barrelled air cannon of FIG. 1.

With reference to FIGS. 1 and 2 of the drawings, there is shown a schematic representation of a multi-barrelled air cannon 10 of a preferred embodiment of the present invention.

In a preferred embodiment, a breech chamber 12 (which essentially is an air expansion manifold) is bifurcated into identical first and second barrels 14, 16 each having a muzzle end 18. Relative to a nominal centre line 20 through a major axis of the multi-barrelled air cannon 10 that centrally dissects the breech chamber 12, the angular offset a of each of the first and second channels is typically in the region of between about five degrees and ten degrees and preferably about eight degrees. The volume of the breech chamber is made as small as possible in order to channel energy from the expanding volume into the barrels 14, 16.

Conventionally, the barrels 14, 16 have a generally circular cross section. The barrels 14, 16 are typically of a similar overall length to the length of the breech chamber 12. The barrels may include internal rifling and can be considered as a high precision firing tube.

A backstop 22, such as a detent or a physical constriction within the barrel, defines a loading point past which a bullet-shaped projectile (which acts as a drag weight) 24 cannot pass. The backstop 22 therefore prevents the bullet-shaped projectile 24 from entering the breech chamber 12. An end 26 of the breech chamber (remote to the barrels 14, 16) is coupled to and is in selective fluid communication with a pressure vessel 28; coupling is through a poppet valve described below and shown in FIGS. 4 and 5. The projectiles 24 are, in use, muzzle-end loaded and are dimensioned such that they slide within the barrel whilst minimizing the ability for air leakage around a base of the projective. Air leakage around the end of the projectile may be mitigated through the use of wadding material used as a packing. Other shapes of projective are possible.

The term "projectile" can also be interchangeably referred to as "shot weights", "slugs" and the like.

Each projectile 28 also includes a tether or "dynamic drag" line 50 that flows out from each muzzle end 18 of each barrel. The drag line 50 is securely attached to different ends of a lightweight by strong net 52 that is preferably stored in a cradle, housing or payload storage bucket 54 slung beneath and potentially physically attached to the barrels 14, 16. The drag line 50 is dynamic in nature since it has a connection length of about five meters and it has a stretch factor of typically about 30% to 35%, with this connection length and stretch factor reducing initial in-line stress levels that occur when the projectiles are initially accelerated out of their respective barrels. The drag line 50 is therefore of a length sufficient to prevent the drag line from snapping at the point of deployment and provides a gradual energy delivery system. The net 52 may therefore be a gossamer net made from a natural or synthetically strong and lightweight fibre. The net 52 is folded (and therefore stored and loaded) using known techniques that ensure rapid and unhindered free-lateral expansion.

The angular splaying of the barrels is related to ensuring effective net dispersion and thus the barrels may, in one embodiment, be pivoted so as to alter their angle to alter the range of the air cannon with respect to effective net deployment. The angular splaying of the barrels is therefore also intrinsically associated with the amount of kinetic energy imparted onto the pressure vessel to the projectiles and, therefore, also the mass of the projectiles. The first and second barrels 14, 16 may be angularly separated relative to one another by between about ten degrees and forty degrees and most preferably by between about fifteen degrees and twenty-five degrees.

The pressure vessel 28 is retained within a frame 30 encompassing a recoil mitigation system. The frame 30 is realized by a retaining wall 32 that is fixedly attached to the pressure vessel and is therefore an integral part of the recoil force path. Multiple linear slides 34, 36 (of which two are shown in FIG. 1) extend along the sides of the pressure vessel and are each attached to the retaining wall 32 through a securing nut 38 (or the like). The linear slides attach the air cannon to a frame 55, such as a UGM that is itself coupled to a hull 57 of a RIB.

Typically, a poly bush 40 surrounds the end of the linear slide 36, 38, the poly bush 38 sandwiched between the retaining wall 32 and a recoil mitigator 40, preferably realised by a simple recoil spring 42 or otherwise by a hydraulic or pneumatic cylinder into which the liner slide takes the form of a piston. The recoil mitigator 40, e.g. the coil spring wound around each linear slide, therefore allows compressive movement of the recoil mitigator 40 towards the frame 55; this means that the pressure vessel 28 is displaced from the frame 28 by a distance that cannot be overcome by the recoil force applied through the recoil mitigator 40 and that the retaining wall 32 is always held away from the frame 55 by the action presence of the recoil mitigator 40 (and its dampening effect).

The tension in the recoil mitigator 40 can be varied, e.g. through use of the securing nut and the relative position of the nut on a thread of the linear slide 34, 36. Higher tensions, i.e. greater resistive force, is generally preferred for larger projectile weights, as will be understood.

The pressure vessel 28 has a typical volume of about 5000 $cm^3$, although smaller or larger volumes (±30% or about three liters to about ten liters volume). To keep weight down, the pressure vessel 28 may be constructed from a composite material, such as a carbon fibre with a spun aluminium core of, say, about 0.5 mm thickness. The core therefore acts a former over which the carbon-fibre can be layered to a depth of typically about 2 mm to 3 mm. Alternatively, the pressure vessel 28 can be formed from a suitable plastics material formed in an injection molding process. The barrel may be constructed from a carbon-fibre composite with a stainless steel manifold.

Figure 3:
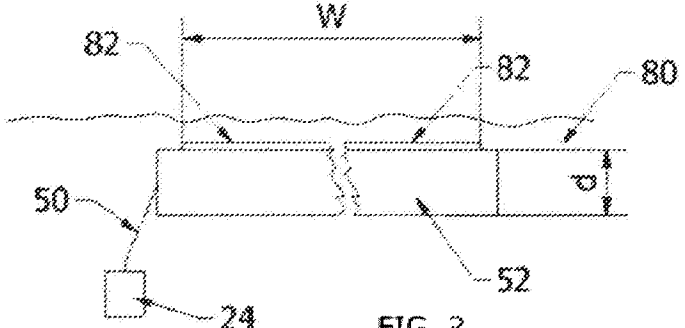
FIG. 3 shows the configuration of a security net of a preferred embodiment, the security net used in conjunction with the multi-barrelled air cannon of FIG. 1.

FIG. 3 show the net 52 in a deployed scenario within a body of water 80. When the air cannon 10 of FIG. 1 is fired, the projectiles emerge from their respective muzzle on a diverging path that extends the net 52. The size of the net is typically in the region of at least one hundred meters in width (w), but could be significantly larger (perhaps 350 m). The net can be several meters deep (d), but is typically around about one meter to about five meters in depth. The projectiles 28 will typically sink to drop the net, buy are of insufficient overall weight to pull the net under. The net 52 may, in a preferred embodiment, include some form of additional floatation device, such as a follow tube, that provides some limited buoyancy to the net 52 to prevent the net from sinking under the weight of the projectiles 28.

The projectiles may be made from metal or a plastic material, such as polypropylene. Typically, the projectiles will have a mass of between about two kilograms and seven kilograms. A mass of about 4 kg is used for a preferred embodiment. Projectile velocity at the point of muzzle egress is in the region of about one hundred and fifty meters per second (150 ms−1). The kinetic energy is therefore typically about forty-five kiloNewtons (45 kN), but is preferred to be always above 10 kN and typically below 60 kN.

Returning to FIGS. 1 and 2, the pressure vessel 28 includes an inlet 90 for an air supply, which inlet 90 is connected via piping to a compressor (not shown) that supplies pressured gas ($P_{gas}$). The piping includes a solenoid 92 having an actuator valve 94, such as a magnetic non-return valve. If connected to the compressor and whilst a positive pressure differential is present, the pressure vessel 28 is charged via the actuator valve 94. A control circuit is configured to permit a small current to cause the solenoid to change the open/closed state of the actuator valve and thereby to allow charging of the pressure vessel or otherwise to trigger a rapid discharge. The configuration of the control circuit and solenoid are well understood to a person of ordinary skill in the art.

Figure 4:
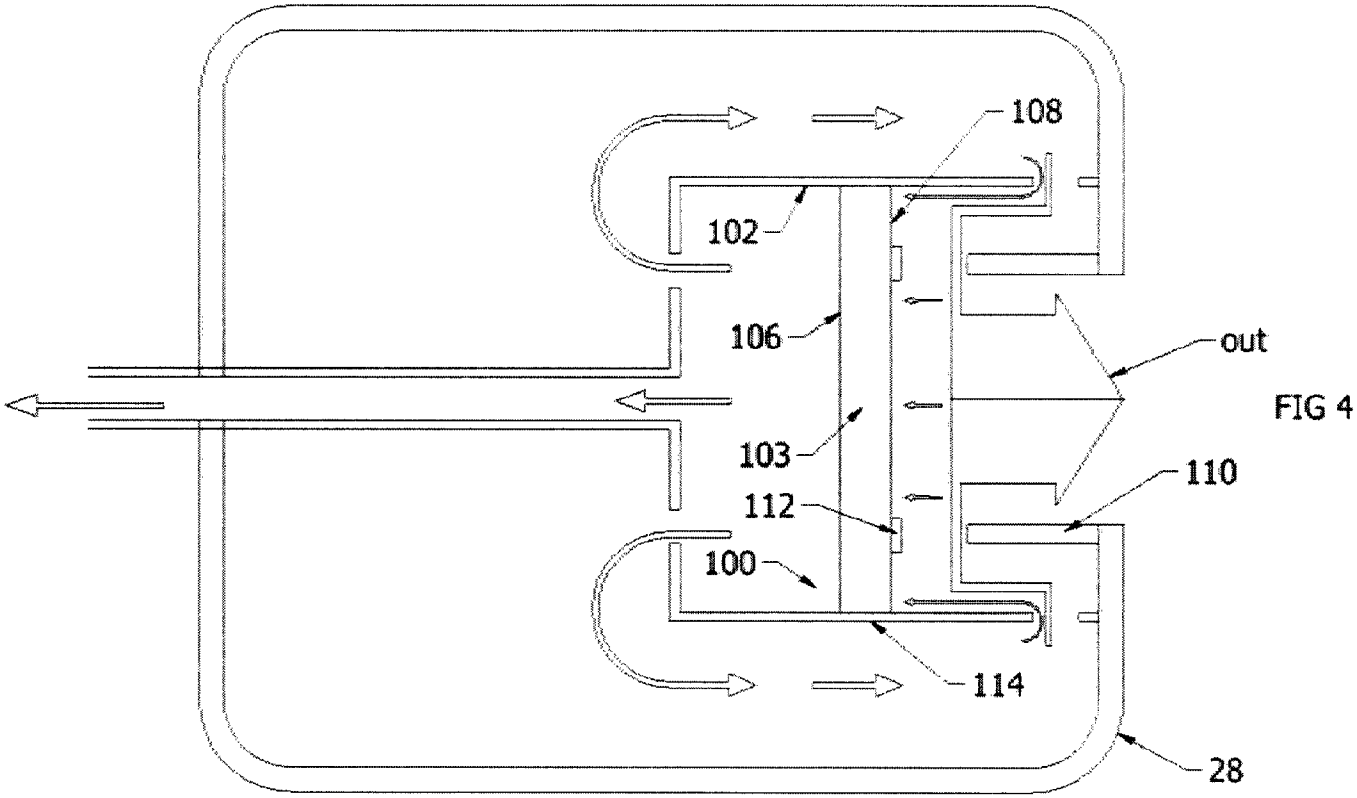
FIG. 4 is a representation of an exemplary pressure vessel including a poppet valve, the pressure vessel employed within the multi-barrelled air cannon of the present invention.
Figure 5:
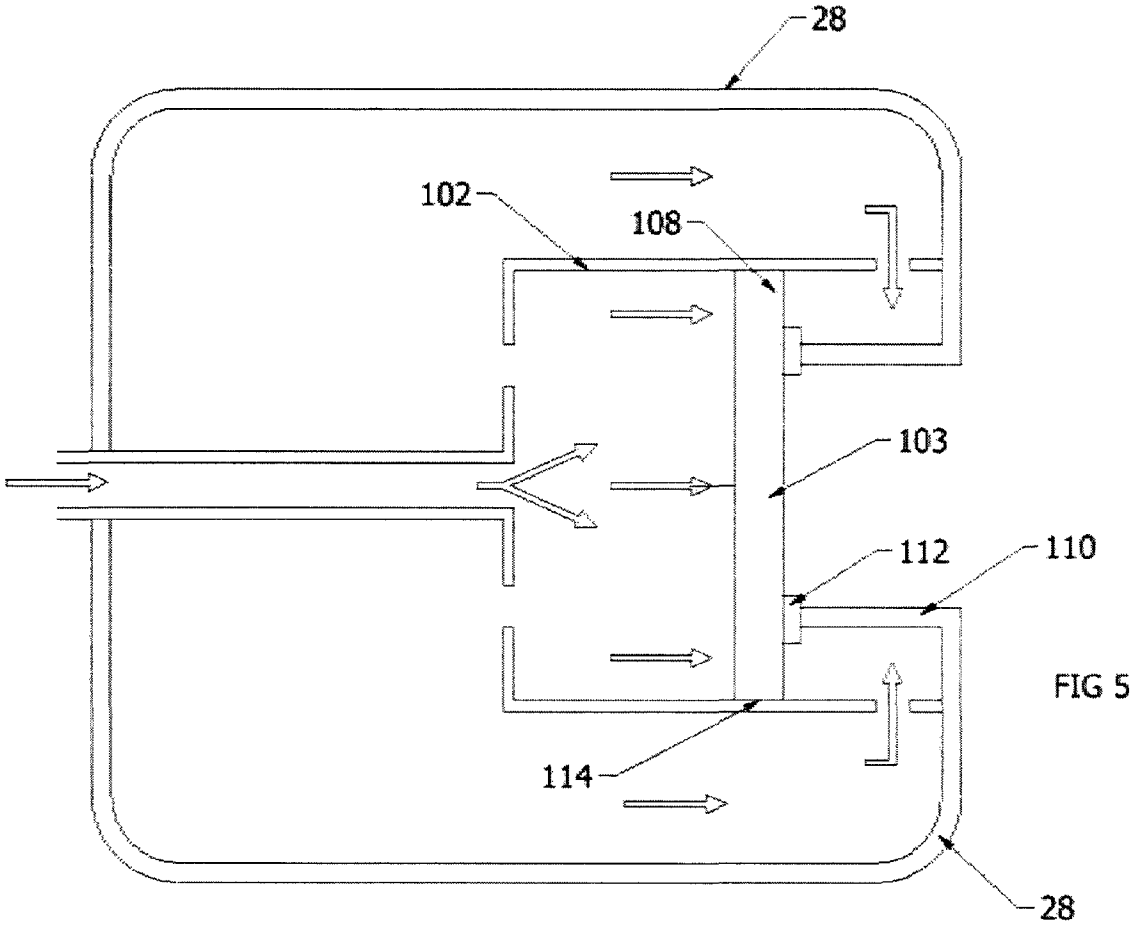
FIG. 5 shows an airflow path within the pressure vessel of FIG. 4, the pressure vessel shown in a closed/charged state.

FIG. 4 shows a representation of an exemplary pressure vessel 28 including a poppet valve 100, the pressure vessel 28 employed within the multi-barrelled air cannon of the present invention. FIG. 5 shows an airflow path within the pressure vessel of FIG. 4, the pressure vessel shown in a closed/charged state.

The preferred pressure vessel 28 contains the inlet 90 that incorporates the actuator valve 94 in its fluid path. A piston 100 is moveable within a volume defined by an internal sleeve 102 within the pressure vessel 29, the internal sleeve 102 in fluid communication with the inlet 90 and its associated valve 94. The piston 103 has an inner surface 106 and an outer surface 108 including an outward contact region, the outward contact region arranged, in use, to abut and seal against a wall 110 of the pressure vessel 28 when the pressure vessel is pressurised and the piston 103 located in a closed position. The wall 110, which may be a right-angled facing lip (relative to the retaining wall 32) is in a major outflow path to the pressure vessel and is therefore coupled to and in fluid communication with the breech chamber 12. Coupling of the pressure vessel 28 to the breech chamber 12 may be through any suitable mechanical coupling and seal, including a gasket and screw thread combination.

The outward contact region may include or interact with an active surface seal 112 that is sandwiched between the outward contact region and the wall 110, which active seal is coupled to one or other of the wall or the outer surface of the piston, whereby the seal accentuates an air-tight seal. The piston 103 typically includes a peripheral edge seal 114, such as a gasket or O-ring, which engages against the inner sleeve as the piston moves along the length of the inner sleeve.

The piston 103, outward contact region and internal sleeve 102 therefore cooperate to define at least part of the poppet valve 100 given that: i) the free-moving piston 103 (see FIG. 5) is pressed into positive air-tight sealing engagement with the wall 110 when pressurised air is introduced into the pressure vessel 28 via the actuator valve 94 and a positive (but at least equal) pressure differential exists between the inner surface and an outer periphery of the outer surface; and ii) the free-moving piston 103 (see FIG. 4) disengages from the wall 110 and seal when the solenoid is momentary energized to open the actuator valve when no compressor gas pressure is acting through the actuator valve 94, i.e. a lower pressure exists on the piston's inner surface 106 relative to that exerted on the piston's outer surface (within the pressure vessel). This minor differential pressure opens the poppet valve 100 and causes balancing of the internal pressure in the pressure chamber towards atmospheric pressure through expansion of gas into the breech chamber 12 and via the barrels 14, 16. In other words, the Y-shaped common breech chamber 12 operates to equalize air pressure expelled from the pressure vessel 28 so that equal force is applied to the rear surfaces of both shot weights. The incorporation of the poppet valve 100 is therefore significant in the context of delivering energy since a poppet valve's operation is nearly instantaneous and is mechanically simple to operate and reset. The energy release is therefore high, with the recoil mitigator 40 cushioning and protecting the mount point of the frame 55 to the RIB.

In summary, a compressor equalized the internal air pressure within the pressure vessel and therefore primes the air cannon. The projectile shots (and attached net) are then loaded. The solenoid (or manually operated valve) is triggered to bring about a slight internal change in pressure across the poppet valve's piston, with this opening the poppet valve and rapidly discharging pressurized gas into the breech chamber. The gas expansion causes the rapid acceleration and ejection of the projectile shots, with the angled nature of the barrels producing a net deployment that yields a security curtain. A recoil mitigator acts to cushion and protect (from recoil forces) any mounting, particularly to a RIB, for a frame to which the air cannon is coupled.

As a failsafe, the compressor may continuously maintain a positive pressure into the inlet to the pressure vessel; this compensates for potential leakages around gaskets and seals in the pressure chamber. Of course, to initiate firing, the pressure is turned off and the poppet therefore allowed to trigger. The predominant discharge is via the main outlet and around the piston, since the actuator valve is only opened for a short period of time.

In another embodiment, the multi-barrelled air cannon may include a third barrel having a third muzzle opening, the third barrel also commonly coupled to the breech chamber. In this configuration, the third barrel (and its projectile's mass) may be used to moderate generally straight line end-to-end deployment of a net otherwise launched solely from the first and second barrels. However, range (for a like-for-like pressure vessel) would be affected because of the additional barrel and additional mass that must be accelerated.

In another embodiment, an air cannon (with a poppet valve) may be implemented with a single barrel that projects a floating line with a drogue at either end. Once deployed, the floating line fouls the stern gear on a boat, and furthermore may transfer the motion to the two drogues which inflate and impart considerable drag on the boat via the floating line thus slowing the boat to a virtual standstill.

The multi-barrelled approach may also make use of drogues employed within the net.

Figure 6A:
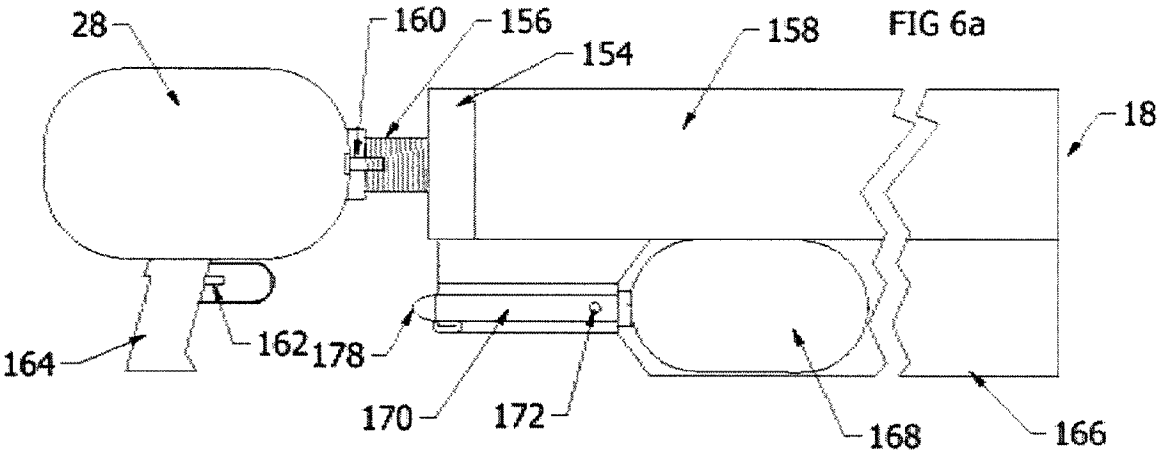
FIGS. 6a and 6b show a single-barrelled air cannon from left and right side views, the single-barrelled [air cannot] *air cannon* in accordance with a preferred embodiment.
Figure 6B:
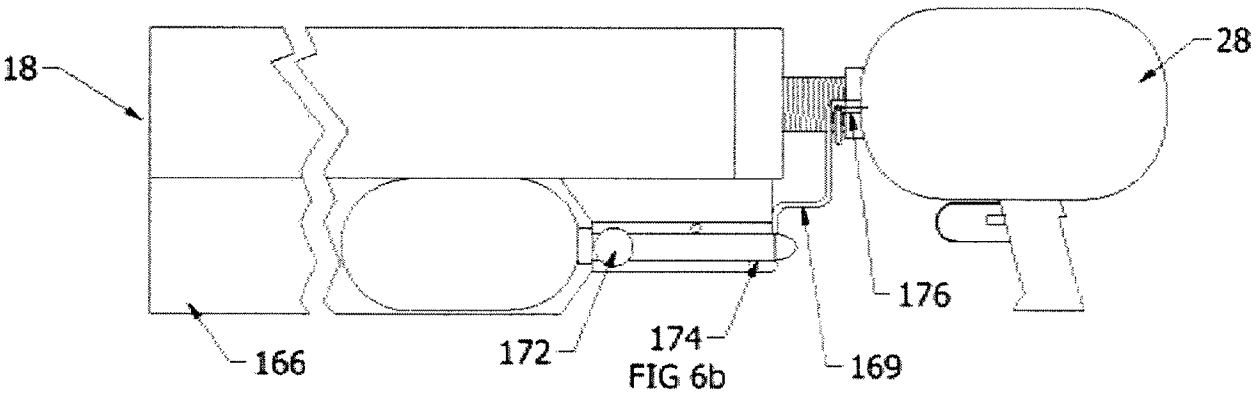

FIGS. 6a and 6b show a single-barrelled air cannon 150 from left and right side views, the single-barrelled air cannon 150 in accordance with a preferred embodiment. Like the aforedescribed multi-barrelled systems, FIGS. 6a and 6b preferably make use of the poppet valve system (of FIG. 5). In contrast with the dual-barrel system of FIG. 1, the arrangement of FIG. [6] *6a and 6b* includes only active energy barrel 156 coupled through a breech chamber 154 (i.e. the air expansion manifold) to the pressure vessel 28. The breech chamber 154 may be within the base of the barrel 156 or realized as a separate component within the fluid path between the pressure vessel and the barrel. A threaded connector 156 preferably permits securing of the manifold-end of single barrel 156 to a regulated, trigger-controlled outlet of the pressure vessel 28. The outlet may optionally include a safety valve 160 configured to avoid over-pressure in the pressure vessel 28.

Figure 7:
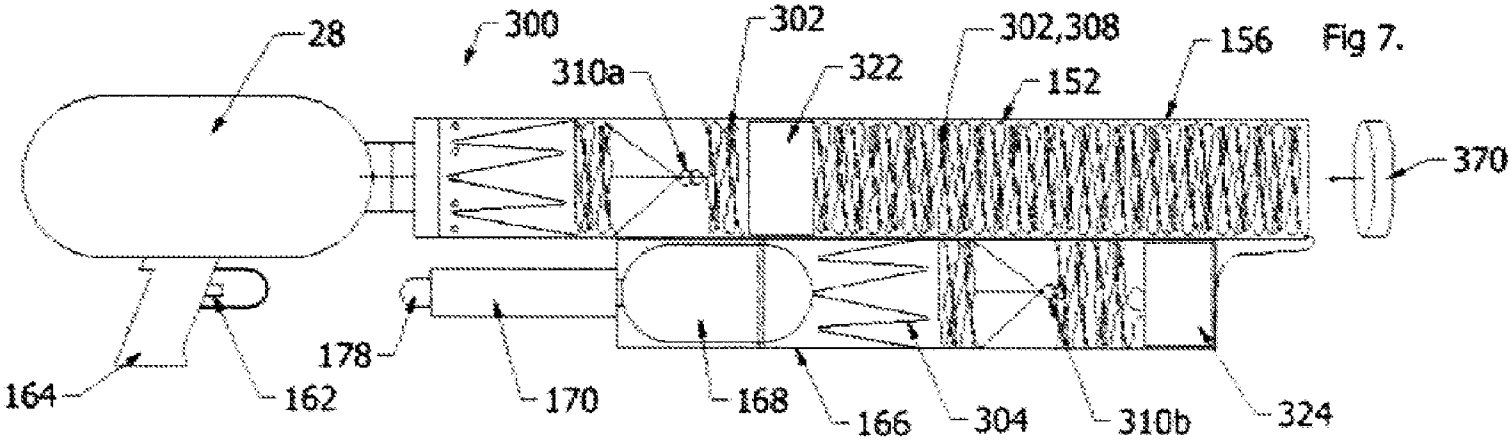
FIG. 7 is a cut-away view of the single-barrelled air cannon of FIG. 6, including a preferred launch canister system—loaded within its barrel and cradle—realised by a prop fouling line loaded in accordance with a preferred packing regime and a launch tube.
Figure 8:
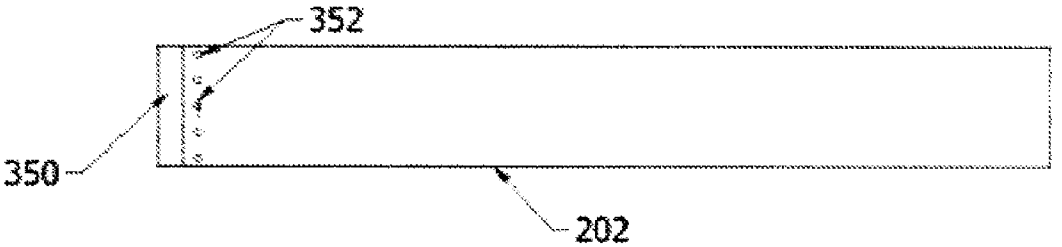
FIG. 8 shows a preferred embodiment of the launch tube of the launch canister system of FIG. 7.

A trigger mechanism 162—of a construction readily understood to the skilled addressee—in a handle 164 permits controlled discharge, i.e. opening, of the poppet valve to cause rapid expansion of pressurized gas through the breech chamber, thereby providing an active driving force that acts on a driving disc 350 at a generally closed base of a launch tube 202 (shown in FIGS. 7 and 8). Typically, the handle 164 is coupled to an underside of the pressure vessel 28. The configuration and use of the launch tube will be described in greater detail below with particular reference to FIGS. 7 to 9.

Returning to FIG. [6] *6a and 6b*, in operation, the barrel is arranged to receive the launch tube 202 containing one end of the prop fouling line (and at least one drogue). Additionally, since the launch tube stores a first end of a deployable floating line (or net), the air cannon of FIG. 6 preferably includes an under slung hopper (or cradle) 166 that stores a second end of the deployable floating line through an open front end (proximate to the muzzle 18 of the barrel). The hopper 166 is securely attached to the barrel and typically tubular in nature. The hopper 166 may itself be realised by a tube.

If the hopper 166 is connected to a pressure vessel (as shown in FIG. 1), the system becomes multi-barrelled. Otherwise, the hopper is simply a storage device conveniently located proximate to the muzzle of the barrel, which storage device supports rapid and unencumbered run out of the prop-fouling line.

In a preferred embodiment, the floating line is made from a lightweight, strong and typically multi-filament fibre, such as Dyneema® cord or Spectra® cord, that has a high strength-to-weight ratio. Other fibres, including man-made ultrahigh molecular weight polyethylene("UHMWPE") materials or natural materials (such as silk) may be used to produce the snagging line, cord or rope. The terms "cord", "line" and "rope" are therefore interchangeable and functionally equivalent names may also used.

Physical parameters for the fibre require that its construction must be such as to resist catastrophic fraying potentially encountered as the line is drawn along the generally submersed hull of a boat from bow to stern. Second, the strength of the cord must be sufficient to resist being snapped when a laterally deployed cord is tensioned by the initial ongoing forward motion of the boat. Once the cord is snagged by the hull or propeller, drogues at either end of the cord act as sea anchors in that they scoop up water to resist angular movement and physical displacement from their deployed positions; again this will be explained in more detail later.

It is noted that, given the high speed nature of the craft/boat that the security curtain system is designed to restrain, these craft are generally flat-bottomed with no significant keel. However, the system may also snag in the keel to effect boat slowing through drag.

Returning to FIG. 6, the hopper 166, at its distal end nearest the pressure vessel 28, preferably includes a high pressure (storage) gas cylinder 168 networked through valves, ports and piping 169 to the pressure vessel 28. More specifically, the gas cylinder acts as a charging reservoir for the pressure vessel 28 and has a capacity for, typically, supporting multiple consecutive shots. In a flow path between the gas cylinder and pressure vessel, a preferred system will typically include at least a gas pressure regulator 170 and gas pressure gauges 172, 174 for monitoring gas cylinder pressures and regulated pressure. The gas pressure regulator acts to reduce the pressure delivered to the pressure vessel from, say, about 200 bar (20 MPa) to about 10 bar (1 MPa).

A controllable fill valve 176 provides control of gas connection, via the piping 169, between the storage gas cylinder 168 and the pressure vessel 28 (charged by gas in the storage gas cylinder). The storage gas cylinder 168 may be positively engaged by a releasable locking brace or the like.

A bleed valve 178 is provided to relieve line of pressure after filling and before disconnection (of the gas cylinder 168).

The pressure chamber 28 may have a working pressure of 45 bar (4500 kPa), but lower working pressures are preferable for handheld application, e.g. 10.3 bar (1030 kPa). Metal components in the pressure chamber are generally constructed from corrosion resistant stainless steel. Operational pressures depend on the construction limitations of the pressure chamber 28 as well as shot weight/delivery distance requirements. Also, a large safety margin is preferred between theoretical operating pressures and actual operating pressures because of both rapid de-pressurization and the cyclic nature of the operation of the air cannon.

The storage gas cylinder does not need to be integrated with the air cannon and is merely a design preference to allow for rapid local re-charge without recourse to external equipment.

FIG. 7 is a cut-away view of the single-barrelled air cannon of FIG. 6, including a preferred launch canister system 300—loaded within its barrel 158 and cradle 166—realised by a prop fouling line (reference numeral 302 of FIG. 9) loaded in accordance with a preferred packing regime and a launch tube 202 (FIG. 8).

FIG. 8 shows a preferred embodiment of a launch tube or launch canister 202 of the launch canister system of FIG. 7, and FIG. 9 shows a preferred configuration of a prop fouler according to the present invention. The launch canister 202 may be considered to be a munition casing.

Starting with the prop-fouler 300 of FIG. 9, this is preferably realised by a strong lightweight cord 302 having a length of at least forty meters and typically up to about 150 meters; other lengths are also possible and depend on the application and available pressure. The cord 302 preferably floats by virtue of its own construction/physical properties, although the cord may optionally or necessarily include additional buoyancy aids to produce a near-surface or on-surface floating position when it is deployed in water. Of course, a lightweight cord is optimal because of packing thereof into the launch canister.

Each end of the cord 302 terminates in a drogue 304, 306. Each drogue includes an enclosed volume typically produced in the form of an open-based polyhedral or a cone having an open mouth and a closed apex. Other shapes are possible. The drogue is typically made from a strong woven material or the like and is shaped to act as a parachute sea anchor. The wide mouth region allows fluid to enter into the entraining void of the drogue to weight down the drogue and produce drag.

Coupling of the drogues 304, 306 to either end of a main central body region 308 (constituting the majority of the overall length of the prop fouler 300) of the cord is via a rotating shackle 310 that serves at least three purposes. First, each rotating shackle 310 acts as a weight that encourages a neck of end of the drogue to be pulled down into the water. In this respect, the rotating shaking 310 is relatively heavy and typically made from a ring of corrosion resistant steel. Second, each rotating shackle 310 permits the main central body region of the prop-fouler 308 to be able to twist independently of each drogue 310. Third, with each drogue attached to the rotating shackle 310 about an annular ring and through multiple strong shroud lines 312, the rotating shackle 310 prevents chafe and enables the rotating shackle to swivel, to work without restriction and to resist twisting of shroud lines 312 by providing a wide spread of these shroud lines. The physical arrangement of the rotating shackle 310 acts to absorb shock loads without blowing panels or twisting shroud lines 312; this means that the drogue will generally not be susceptible to collapse. A suitable self-adjusting rotating shackle 310 is the Para-Ring® by Fiorentino, as described in US design patent D492, 576-Fiorentino et al.

It is noted that the attachment of the shroud lines 312 to the drogue preferably occurs along reinforced edges (or seams) 314 of the drogue's canopy, with the shroud lines generally evening spaced about the drogue's canopy and passing commonly through an apex 318 in the drogue canopy. The reinforcement of the canopy along certain seams or regions encourages the canopy both to deploy and remain open when subject to drag. Canopy volume of the drogue will vary and is matched to the strength of the cord 302. As will be understood, the larger the canopy volume, the higher the drag and the more strain induced during drag. Canopy volumes are typically in the region of about 3 to 5 gallons (i.e. about 13000 to 20000 cubic centimeters), although larger and smaller drogues can be deployed. Indeed, in one particular embodiment, multiple small drogues (of say 5000 cm3 each) may be employed at each end of the prop-fouler 300.

For a 13000 cc drogue, the apex 318 of the canopy is separated from the rotating shackle by between about one and two meters. Other separation distances are possible and can be determined empirically.

The prop-fouler 300 is somewhat asymmetric in design in that a front float 322 provides a degree of movable mass to a lead end of the prop-fouler 300. The front float is located proximate to a first rotating shackle 310 a, e.g. within about one meter, and inward of the shroud lines. The front float acts as a projective mass to encourage straight line extension of the cord 302 from the point of release. A secondary tail float 324 may be smaller and lighter than the front float 322, but may also be similarly sized. The secondary tail float is similarly positioned at a distance of typically less than a meter relative to the second rotating shackle 310 b at the rear-end of the prop-fouler 300. The secondary tail float 324 only needs to provide line buoyance shortly before prop-fouling occurs.

Front and tail floats, whilst preferred, are optional. Floats that are inboard of the rotating shackle metalwork permit the drogue canopy to inflate in a downwards direction, but they also present the cord 302 (of the prop-fouler) to the target in an optimal way.

These inboard floats 322, 324 are preferred, but optional. Once immersed the canopy of the drogue acts to provide a degree of floatation to offset the weight of the rotating shackle. The weight of the rotating shackle, however, causes the drogue to be pulled under the water and to fill through its open neck (maintained open by operation of the para-ring, i.e. the rotating shackle 310).

Returning to FIG. 8, a preferred configuration of a launch canister 202 for the prop-fouling system is shown. The launch canister 202 is tube-like and fits into the barrel 156 of the air cannon like a loose sleeve, i.e. there is a small degree of clearance to allow movement, with the clearance relatively small so as to limit the amount of high velocity air from escaping from about the launch canister (after opening of the poppet valve). The launch canister 202 therefore acts, initially, as a casing for the crop-fouling cord. Unlike a bullet, the launch canister is a detachable fairing that, after firing, is designed to separate from the crop fouler 300.

The launch canister 202 has a length that is preferably about the same overall length as that of the barrel 156, although other lengths are possible. At a closed base of launch canister 202, a driving disk (or driving plate) 350 provides a sturdy and robust reaction surface upon which high velocity pressurised air can act to project the sleeve forward and outward of the barrel. The launch canister 202 is generally made from a composite material that floats, although the driving disk 350 may be metal.

Proximate to the driving disk 350, a row of circumferentially-spaced ventilation holes 352 penetrate the sleeve. These ventilation holes 352 are present to aid in drogue deployment by avoiding the creation of negative pressure when the lead drogue 306 is withdrawn from the launch canister 202.

Returning to FIG. 7, packing of the launch canister 202 with the prop-fouler 300 is shown in situ within the exemplary context of the single barrelled air cannon of FIG. 6.

Preferably, lead drogue 306 is loaded closest to the driving disk 350. In order, the shroud lines 312, rotating shackle 310a and front float are then stacked. Between the front float 322 and an optional (but preferred) lightweight retaining bung 370 that loosely fits into the top, open end of the launch canister 202, the cord is suitably coiled for rapid deployment. The retaining bung 370, made perhaps from expanded polystyrene, does not need to be part of the prop-fouling line and is present only to initially hold the cord 302 in place and to keep the inside contents of the launch canister both generally dry and generally clean. Most of the length of the cord 302 is therefore retained in the launch canister, save for a small length that runs external to the launch canister 202 towards the hopper/cradle 166.

Loading of the front drogue, etc. into the launch canister may make use of a ramrod.

With respect to the cradle 166, this holds the tail float 324 and packs, rearwardly of the tail float, the rotating shackle [302b] *310b*, the shroud lines 312 and the (tail) drogue 304. As indicated, the storage gas cylinder 168 may be conveniently located at a distal end of the cradle 166.

The function of the launch canister is to protect the cord from the initial pressure discharge (acting against a rear surface of the driving disk 350) and to ensure that a dominant direction of travel is established for the launch canister and its contents. The launch canister also prevents the prop-fouling cord from snagging in the barrel and protects the cord from the effects of frictional heating that might impair egress from the barrel. It has been identified that the launch canister 202 increases the deployment range of the prop-fouler.

In adopting the packing regime for the prop-fouler 300 as especially shown in FIG. 7, opening of the poppet valve to release high pressure air accelerates the launch canister smoothly out of the barrel 156. The loaded air cannon is preferably shoulder-fired at an angle of about thirty degrees to the horizontal (30°). The prop fouler is deployed in front of the target vessel. Run out lengths for the prop fouler cord/cope are typically from about twenty meters to about three hundred meters (or more) and more preferably in the range of between about at least fifty meters and two hundred meters. Other lengths are possible, with deployed extension depending upon a number of factors, including (but not limited to) available energy stored in the pressure vessel, weight of the prop fouler and firing angle. In general, the length of the prop fouler must be sufficient so as to permit rapid deployment in front of a moving boat that is to be retarded, and of sufficient length to avoid that boat from undertaking evasive manoeuvering.

While not wishing to be bound by theory, upon exiting the barrel at considerable velocity, a combination of one or more of the canister's weight distribution, its aerodynamics (from the perspective of an open-ended tube) and the tethering to a stationary tail end (held in the cradle and not subject to acceleration) cause the launch canister to flip about 180 degrees; this means that line is deployed rearwardly from the open end of the launch canister 202. At some point, the portion of the prop-fouler held in the cradle 166 is pulled out of the cradle, with this action then causing the drogue to deploy temporarily as an air parachute brake. Firing results in the front drogue (and the launch canister) being propelled forward from the air cannon's barrel, with deployment of the tail drogue marginally delayed (and subject to a snap-pull event).

The initial air drag from the tail drogue 304 and/or its immersion in water pulls the front drogue free of the launch canister 202 at the point when the length of the prop-fouling cord is run out. Relative inertia effects may also cause release of the front drogue from its protective canister 202. The weight of the rotating shackle and front drogue cause the front line to fall under gravity and to hit the water and the to sink. Projection of the launch canister and the drag effect from the tail drogue contribute to produce a generally straight (but at least controlled) deployment of the floating prop-fouling line.

Separation of launch canister 202 means that it can then be recovered and re-used.

Consequently, as a boat's hull runs over the deployed prop-fouling line, the boat's stern gear snags the line. The snagged line pulls on both drogues 304, 306 to fully inflate them and to create a large amount of drag through production of sea anchors. Empirical results show that two 13000 cc drogues have sufficient drag resistance to retard sufficiently a fast moving boat down to walking pace. Advantageously, the use of a single line provides a considerably longer entrapment device than a net fired from the same launcher.

Rather than packing the launch tube as shown in FIG. 7, the launch canister can be packed with the majority of the lightweight (snagging line) cord proximate to the driving disk 320. The front drogue may then act as a sealing bung for the launch canister since the front drogue 30 is adjacent the opening of the launch canister. In this configuration, a length of cord 320 necessarily runs back along an inner surface of the launch canister and then out of the end of the launch canister. The configuration, however, has been empirically assessed to be less efficient in terms of distance achieved following firing. Without being bond by theory, additional frictional forces experienced with the feeding out of the cord past the front drogue are believed to impair flight.

From an assembly perspective, the launch canister is loaded and assembled in the following preferred fashion:

- The front drogue is folded tightly and inserted into the launch canister using the ramrod to ensure it is fully loaded at the bottom of the launch canister near the driving disk 350.
- The shroud lines 312 and front rotating shackle 301a are pushed into the canister 202 followed by the lightweight prop-fouling (e.g. multi-strand Dyneema) cord.
- The cord is frequently tamped down as it is fed into the launch canister
- A quick release adhesive tape may be used to hold the end of the cord in place.
- The launch tube can then be loaded into the barrel of the air cannon (of, for example) FIG. 6. Loading is nose first.
- The tail drogue is tightly folded and inserted into the under barrel hopper together with the shroud lines and associated swivel assembly.
- The hopper is plugged with the front float.
- The pressure vessel 28 is now ready to be pressurized and fired.

Each of the various embodiments of the invention may, in fact, include a sealable and selectably operable valve in the breech chamber 12 (i.e. the air expansion manifold). Basically, the valve (of well-known configuration, such a semicircular vane) can be opened to shut by manual or electrical operation, with the valve defining how the expanding air is distributed through the manifold of the air cannon and into one or more of the barrels. For example, in the open position, both barrels would be fired simultaneously, whereas selective rotation and sealing of the valve may allow for the firing of, say, the right or left barrel only. The valve position could then be reversed for the firing of the other barrel (once air cannon has been recharged with compressed air). It will be understood that the valve could be located in a different point within the air cannon, such within each barrel, although realization in the manifold means that energy is not wasted.

Whilst some of the various embodiments make use of the term "prop-fouler", it will be understood that this term should be understood to include line snagging on any or all of (without limitation) a boat's hull (including any keel), its stern gear (including the rudder) and/or the propeller or drive systems. Furthermore, snagging/fouling may foreseeable occur against boat equipment suspended over the edge or trailing from a boat. The term "prop fouler" and the like is functional and broad and not limited just to line arrangements that cause entanglement around the propeller shaft and propeller per se of a boat. Rather, the term "prop fouler" should be understood to include line-based or net-based systems designed to accomplish retarding of the boat of engaging the boat, i.e. "boat foulers" or "hull foulers".

It will be further understood that unless features in the particular preferred embodiments are expressly identified as incompatible with one another or the surrounding context implies that they are mutually exclusive and not readily combinable in a complementary and/or supportive sense, the totality of this disclosure contemplates and envisions that specific features of those complementary embodiments can be selectively combined to provide one or more comprehensive, but slightly different, technical solutions.

It will, of course, be appreciated that the above description has been given by way of example only and that modifications in details may be made within the scope of the present invention. For example, while a preferred embodiment deploys a net, the net could be replaced by a rope, albeit that a rope is a compromise in that it has limited depth beneath the surface of the water. The term "net" should therefore be understood to relate to a structure that expands and extends between the projectiles and which structure acts as a security curtain or prop-fouler and includes equivalent cords and rope-like structures that float at or near to the surface of the water. The terms "net" and "line" and "cord" (and any functional equivalent) are therefore interchangeable, unless the specific exemplary context requires a more limited meaning. Further, whilst the use of the launch canister has been described in relation to a single barrelled air cannon, the launch canister may be used for each barrel in a multi-barrel design, thereby protecting prop-fouling cord or netting.

Although the preferred embodiments described the attachment of the air cannon to a universal gun mount, other mounting arrangement are envisioned (including ground-based frames). Given the energy transfer capabilities realised through the discharge technique that makes use of a poppet valve, the recoil system as described herein is preferable.

The invention claimed is:

1. An air cannon system comprising:

A) an air cannon comprising (i) a *primary* barrel with a muzzle end and a [manifold] *breech* end *remote to the muzzle end*, (ii) a pressure vessel, [(iii) a manifold] coupled, via a valve, [between the pressure vessel and the manifold] *to the breech* end of the *primary* barrel such that the pressure vessel is selectively in fluid communication*, via a connecting breech chamber providing a fluid path between the pressure vessel and the breech end,* with the *primary* barrel through controlled operation of the valve, and ([iv]*iii*) a firing mechanism;

B) a launch [canister delivery system having a] sleeve configured to be slideably loadable [within] *into* the *primary* barrel of the air cannon *from the muzzle end*, the sleeve having a closed end and an open end, the closed end including a driving disk [having an external rear surface]; and C) a floating boat fouling line comprising a major part and a minor part, wherein the major part is packed within the *launch* sleeve [of the launch canister delivery system] and the minor part is kept external to the *launch* sleeve, the floating boat fouling line including:

i) high-strength lightweight cord having first and second ends and a central section therebetween, the central section comprising a first length of the cord and a second length of the cord that end-to-end make up the cord between the first and second ends and where the first length of the cord is more than half of the central section and the second length of the cord is less than half of the central section;

ii) a first rotating shackle and a second rotating shackle, the first rotating shackle coupled to the first end of said cord and the second rotating shackle coupled to the second end of said cord; and iii) a front drogue and a tail drogue, each of said front drogue and said tail drogue including a canopy and each of said front drogue and said tail drogue having multiple shroud lines extending from the canopy thereof;

wherein the shroud lines from the front drogue are attached to the first rotating shackle and the shroud lines from the tail drogue are attached to the second rotating shackle, the rotating shackles arranged both (a) to act as a sink weight to cause, when deployed in water, submersion of each respective canopy, and (b) to isolate twisting of said central section of said cord from twisting of said shroud lines;

wherein the major part of the floating boat fouling line that is packed within the *launch* sleeve includes the front drogue, the first rotating shackle and the first length of the central section of the cord, whereas the minor part of the floating boat fouling line outside of the *launch* sleeve includes the tail drogue, the second rotating shackle and the second length of the central section of the cord, and wherein the closed end of the *launch* sleeve is loaded into the *primary* barrel so that the driving disk is seated adjacent to the [manifold] *breech* end;

wherein the pressure vessel of the air cannon is arranged to store, when the air cannon is primed, at least one charge of pressurized gas to permit firing of the air cannon; and the firing mechanism includes a trigger and the valve, the valve arranged to be controllably opened[,] in response to actuation of the trigger[,] to cause, after both charging of the pressure vessel with said at least one charge of pressurized gas and actuation of the trigger to fire the air cannon, rapid expansion of pressurized gas from the pressure vessel into the [manifold] *primary barrel via the connecting breech chamber*, thereby to cause, in use, high-velocity gas forcibly to act on [the external rear surface of] the driving disk of the *launch* sleeve to accelerate the launch [canister delivery system] *sleeve* out of the *primary* barrel through the muzzle end.

2. The air cannon system of claim 1, further comprising a cradle coupled to the *primary* barrel, wherein the minor part of the floating boat fouling line is loaded into the cradle.

3. The air cannon system of claim [2] *1*, wherein [the cradle is] a secondary barrel *is* located beneath the *primary* barrel, the secondary barrel having an open end and a closed end and wherein the secondary barrel is packed with the minor part of the floating boat fouling line [such that the tail drogue is loaded closest to the closed end of the secondary barrel].

4. The air cannon system of claim [3] *1*, wherein the floating boat fouling line further includes a [rear] *front* float and wherein the [secondary barrel] *launch sleeve* is packed with the [rear] *front* float, *and* wherein the [rear] *front* float is coupled to said cord[, the rear float] *and* positioned adjacent to the [second]*first* rotating shackle and [wherein the rear float is] inboard of the [second] *first* rotating shackle relative to the [tail] *front* drogue.

5. The air cannon system of claim [1] *4*, wherein the floating boat fouling line further includes a [front] *rear* float and wherein the [sleeve of the launch canister delivery system] *secondary barrel* is packed with the [front] *rear* float, [and] wherein the [front] *rear* float is coupled to said cord [and], *the rear float* positioned adjacent to the [first] *second* rotating shackle and *wherein the rear float is* inboard of the [first] *second* rotating shackle relative to the [front] *tail* drogue.

6. The air cannon system of claim 1, wherein the canopies of the front drogue and the tail drogue each have a volume between about 5000 $cm^3$ and about 20000 $cm^3$.

7. The air cannon system of claim 1, wherein the high-strength lightweight cord is made from one of:

a UHMWPE material; and a natural fiber.

8. The air cannon system of claim 1, wherein the *launch* sleeve includes at least one ventilation hole juxtaposed with the driving disk.

9. The air cannon system of claim 1, wherein the front drogue is loaded closest to the driving disk and the first length of the central section of the cord is loaded between the first rotating shackle and the open end of the *launch* sleeve.

10. The air cannon system of claim 1, wherein the *launch* sleeve includes a plurality of ventilation holes juxtaposed with the driving disk.

11. The air cannon system of claim 10, wherein the plurality of ventilation holes are circumferentially-spaced.

12. The air cannon system of claim 10, wherein the cord has a run-out length of the cord from the sleeve, and wherein the run-out length is between about fifty meters and about three hundred meters.

13. The air cannon system of claim 1, wherein the cord has a *run-out* length *of the cord from the launch sleeve,* and *wherein* the *run-out* length is between about [twenty] *fifty* meters and about three hundred meters.

14. The air cannon system of claim 1, wherein the valve in the firing mechanism is a poppet valve.

*15. The air cannon system of claim 1, wherein the pressure vessel includes a fill valve allowing re-charge of the pressure vessel with pressurized gas.*

* * * * *